United States Patent
Zeiss

(10) Patent No.: US 6,776,526 B2
(45) Date of Patent: Aug. 17, 2004

(54) METHOD FOR NAVIGATION-CALIBRATING X-RAY IMAGE DATA AND A HEIGHT-REDUCED CALIBRATION INSTRUMENT

(75) Inventor: Mario Zeiss, Poing (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 24 days.

(21) Appl. No.: 10/134,975

(22) Filed: Apr. 29, 2002

(65) Prior Publication Data
US 2003/0161442 A1 Aug. 28, 2003

(30) Foreign Application Priority Data
Feb. 22, 2002 (EP) .................................. 02003286

(51) Int. Cl.[7] .............................................. G01D 18/00
(52) U.S. Cl. ........................ 378/207; 378/162; 378/164
(58) Field of Search ............................ 378/62, 63, 162, 378/163, 164, 204, 205, 207

(56) References Cited

U.S. PATENT DOCUMENTS

| | | | |
|---|---|---|---|
| 3,577,160 A | 5/1971 | White ........................ | 378/162 |
| 5,784,431 A | 7/1998 | Kalend et al. ................ | 378/65 |
| 5,799,055 A | 8/1998 | Peshkin et al. ............... | 378/42 |
| 5,967,982 A | 10/1999 | Barnett ...................... | 600/429 |
| 6,379,043 B1 * | 4/2002 | Zylka et al. ................ | 378/207 |
| 6,471,399 B1 * | 10/2002 | Zylka et al. ................ | 378/207 |
| 6,584,174 B2 * | 6/2003 | Schubert et al. ............ | 378/165 |
| 6,658,089 B1 * | 12/2003 | Mohr et al. ................. | 378/162 |

* cited by examiner

Primary Examiner—David V. Bruce
Assistant Examiner—Courtney Thomas
(74) Attorney, Agent, or Firm—Renner, Otto, Boisselle & Sklar, LLP

(57) ABSTRACT

A method and system for calibrating x-ray image data for medical navigation using a calibration instrument that is detected and tracked by a medical navigation system and has a plurality of localization structures that are detectable in x-ray images. The localization structures are arranged on at least two spaced supports. The method includes producing an x-ray image without a patient of the localization structures while the calibration instrument is tracked by a medical navigation system. After the x-ray image is registered in the medical navigation system using the localization structures, at least one of the spaced supports is removed from the calibration instrument. A second x-ray image is taken of a patient together with the calibration instrument with the support removed. The two images are compared to determine whether there is sufficient correspondence of the localization structures visible in the two images.

16 Claims, 2 Drawing Sheets

METHOD FOR NAVIGATION-CALIBRATING X-RAY IMAGE DATA AND A HEIGHT-REDUCED CALIBRATION INSTRUMENT

The invention relates to a method for navigation-calibrating x-ray image data and to a height-reduced calibration instrument. In particular, the present invention relates to the field of computer-assisted surgery and image-assisted surgery, wherein a medical navigation system comprising a screen output is available to the surgeon carrying out the treatment, to guide and/or assist him during surgery to be performed.

Within the framework of such medical navigation, it is additionally possible to fall back on information determined from x-ray images produced in situ, wherein on the one hand additional and important anatomical information from the x-ray image can then be introduced into navigation image support, and on the other hand the option also exists of updating registration of the patient in the navigation system, with the aid of the x-ray images.

Such a system is known for example from EP 1 153 572 A1.

Further documents dealing with the technical background of the above-cited "x-ray navigation" are U.S. Pat. Nos. 5,799,055, 3,577,160, 6,118,845, 5,784,431, 5,967,982 and 5,772,594.

Navigation of this kind, assisted by x-ray images, can be used in various medical surgery, for example spinal cord operations and within the framework of accident surgery. This requires both suitable software in the navigation system and a calibration instrument to enable navigation on registered/calibrated image data using an x-ray device, for example a C-arc.

Figure 2:
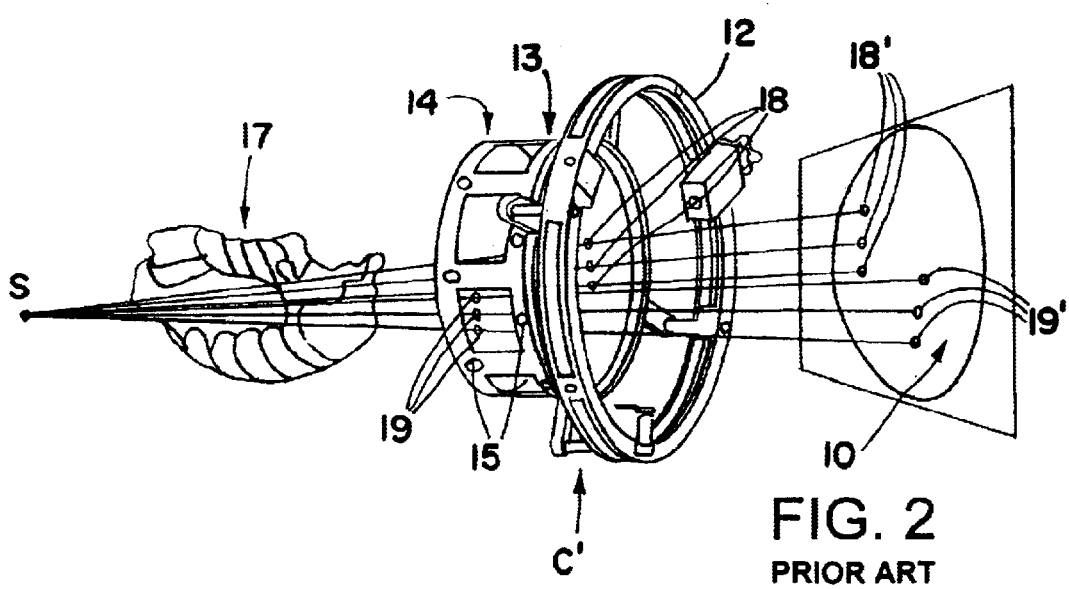
Figure 3:
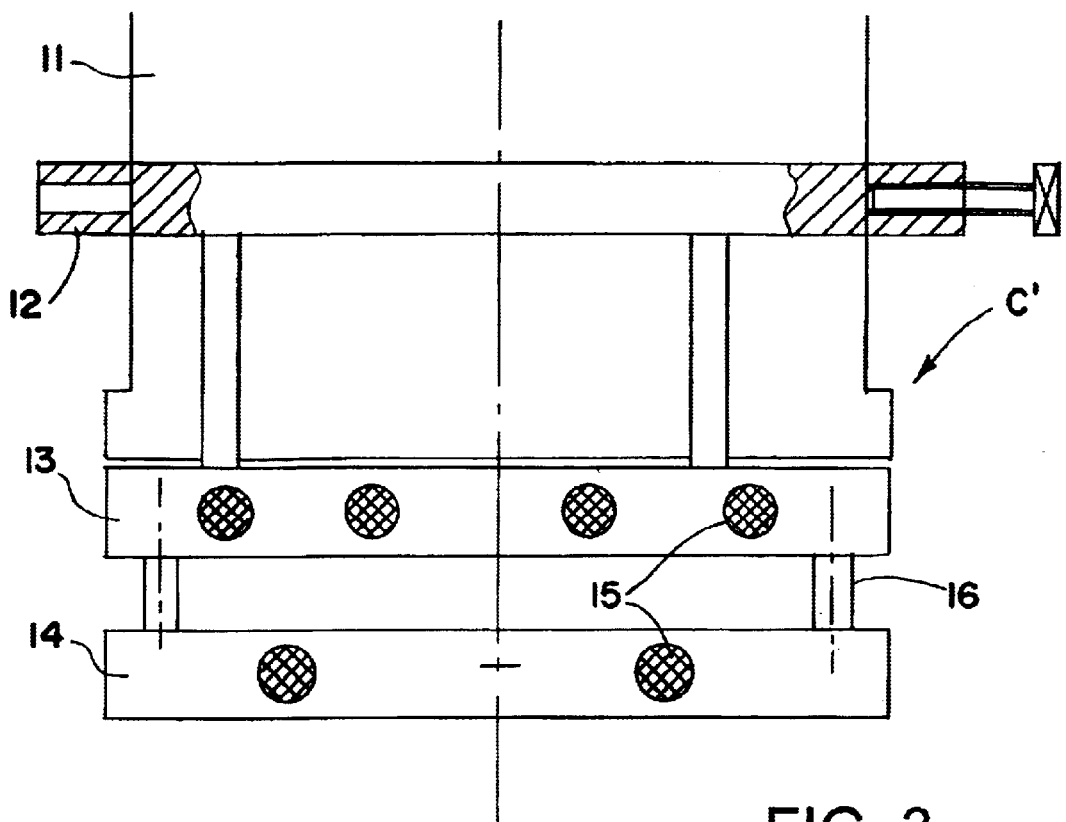

An example of a conventionally used calibration instrument can be seen in the perspective representation in FIG. 2; a schematic vertical section of this instrument is shown in FIG. 3. This conventional calibration instrument C' consists of a fixing means 12, with the aid of which the instrument can for example be attached to the image recorder of a C-arc x-ray device. This image recorder (detector) is only shown in outline in FIG. 3 (reference numeral 11). A first support 13 and a second support 14 are attached to the fixing device 12, spaced successively, and circumscribe plates on which localization information has been placed, i.e. for example, structures in the two plates such as tungsten spheres, line structures, etc., which are used both to rectify the image and to orientate the image. Such a localization structure, i.e. a tungsten sphere, is shown from each of the plates shown in FIG. 2, by the reference numeral 18 (support 13) or 19 (support 14). These structures have a defined arrangement, and the supports and/or plates are also arranged at a defined distance from each other, to enable a virtual radiation source to be calculated which in FIG. 2 is provided with the reference numeral S. The larger the distance between the planes or supports 13, 14, the more accurately the radiation source can be calculated and the more accurate the navigation on the registered image data.

FIG. 2 shows what such an image, i.e. the generated x-ray image 10, could look like. The x-rays travel from the virtual radiation source S through the part of the body to be imaged, a part of a spine 17 being shown in FIG. 2. The x-rays then penetrate the first and second plate on the supports 14, 13 of the calibration instrument C', so as to ultimately provide the image of the spine, together with images 18', 19' of the localization structures, on the x-ray image 10. Since the multitude of localization structures for a particular irradiating angle always accurately provides an assignable image arrangement, the location of the virtual radiation source S can be exactly deduced from the images of these structures. This provides exact knowledge of the orientation of the x-ray image produced.

Sensors and/or markings 15 are additionally situated on the calibration instrument C', which can be LEDs, reflective markers or magnetic sensors, and which enable a medical navigation system to determine the spatial position of the calibration instrument C' with the aid of software. The spatial position of the x-ray image itself can then be determined from the information on the spatial position of the calibration instrument and on the orientation of the x-ray image, and integrated into navigation. FIG. 3 additionally shows, with the reference numeral 16, the connection between the first support 13 and the second support 14, this being a rigid and fixed connection; the two supports 13, 14 are connected to each other as one piece.

When using such calibration instruments within the framework of x-ray navigation, there currently exists the problem that the height of the calibration instrument due to the two supports comprising calibration information, attached at a fixed distance from each other, considerably restricts the "clear width" of the x-ray device. When a C-arc is used, the calibration instrument is sat for example on the image detector and considerably shortens the distance between it and the x-ray generator. This is particularly critical in spinal operations in the lumbar area, but also in hip operations, such that x-ray navigation often has to be foregone in such cases.

It is the object of the present invention to provide a method for navigation-calibrating x-ray image data and a calibration instrument which overcome the above problem; in particular, the option should be provided of forming the clear width of an x-ray device comprising a calibration instrument sufficiently large, to allow x-ray navigation to also be used in hitherto excluded cases.

This object is solved by a method in accordance with the enclosed claim 1 and by a calibration instrument in accordance with claim 8. The invention further relates to a program in accordance with claim 15 and to a computer program storage medium in accordance with claim 16. The sub-claims define preferred embodiments of the invention.

A method in accordance with the invention for navigation-calibrating x-ray image data comprises the following steps:

an x-ray image is produced without the patient by means of an x-ray device into the radiation path of which a calibration instrument is introduced which can be positionally detected and tracked in a medical navigation system;

the x-ray image without the patient is registered in the navigation system with the aid of localization structures arranged on at least two spaced supports of the calibration instrument, and images of the same on the first x-ray image;

a support, together with its localization structures, is removed from the calibration instrument;

a patient x-ray image is produced;

the calibration information from the images of the localization structures of the remaining support on the instrument are compared for the two x-ray images, and calibration is corrected if there is an insufficient correspondence between the images.

The particular advantage of the method in accordance with the invention lies in removing at least one support, together with its localization structures, from the calibration instrument and then compensating for the lack of information thus arising. These measures enable x-ray images to be navigation-calibrated even in cases where a very large clear width or a very large distance between the x-ray generator and the x-ray detector is required, i.e. for example in spinal operations in the lumbar area or also in hip operations. For the first time, the invention shows a way in which, by suitably designing the calibration instrument and suitably using it within the framework of the method in accordance with the invention, x-ray navigation can also be used in operations for which such assistance has hitherto not been possible.

In an embodiment of the present invention, the x-ray image without the patient is produced first, to base-calibrate the x-ray image. Using such a so-called "blank shot" with the two supports of the calibration instrument, the image orientation and/or location of the virtual radiation source for the x-ray device used, which is preferably a C-arc x-ray device, can be determined even before the image with the part of the patient's body is actually produced, in this way, there are no obstacles in the radiation area, such that it does not matter if the clear width between the x-ray generator and the x-ray detector is restricted.

Such a "blank shot" can, however, also be used within the framework of the invention when the physician carrying out the treatment determines that parts of the localization structures are obscured in the x-ray image with the patient, i.e. when the patient x-ray image was taken, such that the image orientation can no longer be clearly determined. A new blank shot then enables the- system-to be accurately re-calibrated.

In the method in accordance with the invention, the calibration information from the images of the localization structures of the remaining support on the instrument is compared for the two x-ray images (with and without patient), and calibration is corrected if there is an insufficient correspondence between the images. A number of options are available within the framework of the invention for such correcting and/or compensating.

The first correcting option is re-calibrating by means of an x-ray image without the patient, preferably with the x-ray device in the same position as when the patient x-ray image was taken. C-arc x-ray devices in particular may have different relative positions of the x-ray generator and x-ray detector in different applications. This positional relationship may be different when the C-arc is aligned horizontally than when the C-arc is placed vertically. This circumstance could lead to distortions which would cause errors in determining the orientation of the x-ray image. Thus, if for example a vertical C-arc is used for the blank shot or for base-calibrating, it may happen when the C-arc is used horizontally that the images of the localization structures of the remaining support on the instrument are shifted in the image with the patient. In accordance with the above-cited embodiment, simply re-calibrating in the same position as in the patient x-ray image would then re-create a suitably calibrated system.

A second correcting option is to calculate, with computer assistance, the change in the imaging position from the change in the image data, new image data for the localizing devices of the removed support then being determined for the imaging position of the patient x-ray image. In other words, the shift in the images for the removed support is also determined or reconstructed by calculation from the shift in the images for the fixed support. Given suitable computation and accuracy, such a system spares any, possibly awkward, re-calibration measures.

In a third possible scenario, a deviation value is determined from the insufficient correspondence, and if this deviation value does not exceed a predetermined limit, the current calibration is taken as the corrected calibration. Thus, if it is established that there is only a slight deviation within the context of the predetermined tolerances, it is possible—without fear of problems—to continue to use the calibration already performed (blank shot, beforehand). The positions for the images of the removed support are simply taken from the blank shot.

A fourth possibility is to determine the corrected calibration from the deviations, based on an interpolation rule determined for the x-ray device beforehand. This advantageously utilizes the fact that a particular x-ray device and/or a particular C-arc is very likely to always show the same deviations, in various applications. These deviations can be detected beforehand, and this knowledge can then be used to determine the correction and/or compensation in particular applications. Lists of pairs of values or an empirically determined function may be used to interpolate.

The calibration instrument in accordance with the invention for navigation-calibrating x-ray image data comprises: a device for arranging the calibration instrument in the radiation path of an x-ray device; at least two spaced supports on which localization structures are provided which are imaged on the x-ray images of the x-ray device; and markings for detecting the calibration instrument using a medical navigation system. It is characterized in that at least one of the supports may be removed from the calibration instrument. By designing the calibration instrument in this way, in particular by making one of the supports for the localization structures removable, a height-reduced calibration instrument is provided which exhibits a sufficiently large clear width, even in hitherto problematic applications. The advantages described above for the method in accordance with the invention naturally apply also to the height-reduced calibration instrument in accordance with the invention.

In accordance with an embodiment of the instrument, the localization structures are formed by spherical or line structures, in particular made of for example tungsten, which may be imaged using x-rays. The calibration instrument can advantageously be arranged on an image recorder of an x-ray device, in particular of a C-arc x-ray device.

The removable support is advantageously arranged on the non-removable support by means of a quick-release lock; said quick-release lock can be a rotating bayonet lock or a plug-type connection. What is important here is that the connection allows each removable support to be accurately positioned and repositioned, in order to guarantee the accuracy of the calibration steps.

In an advantageous embodiment, the markings for detecting the calibration instrument using a medical navigation system are arranged on the non-removable support or the device for arranging the calibration instrument in the radiation path of the x-ray device. The latter device can be the fixing device with which the instrument is fixed to the image recorder of the x-ray device. When some or all of the supports are removed, another embodiment proves particularly advantageous, in which the markings are provided on separate base layers, e.g. adhesive films, which can be attached to the x-ray device itself, in particular to the image intensifier/detector. This embodiment is preferably used when pre-calibration has been performed, and in particular when the corrected calibration is determined via interpolation rules.

Figure 1:
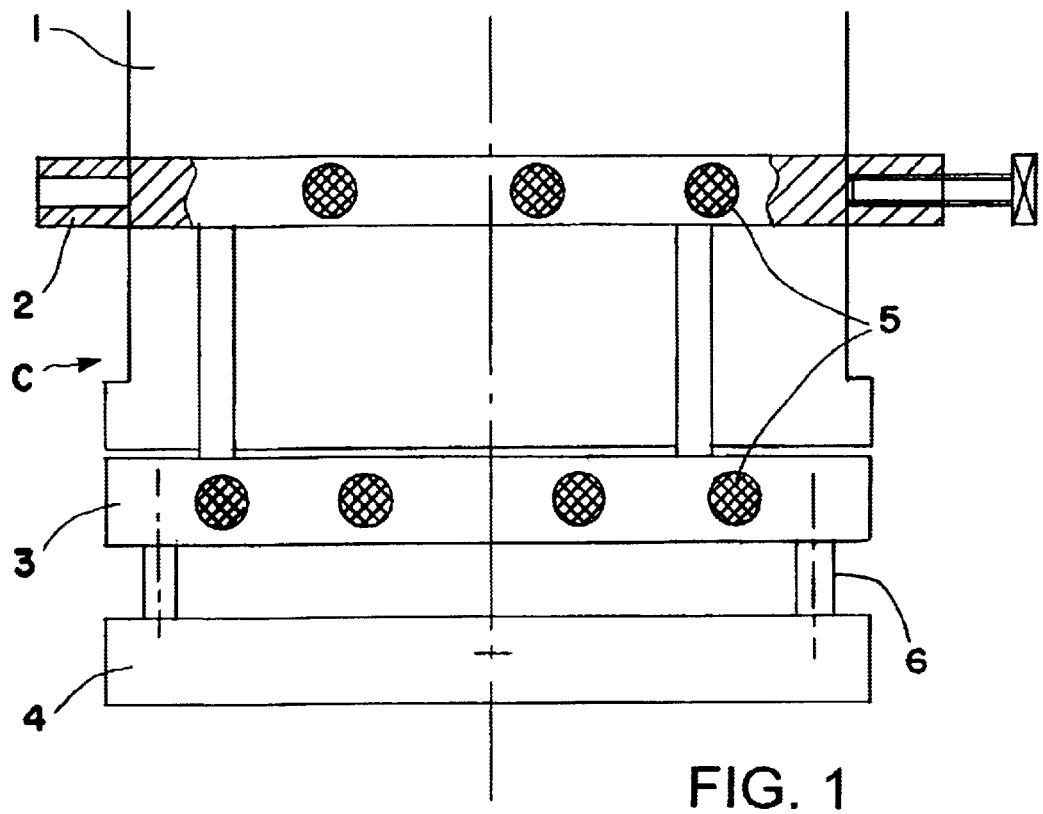
Figure 4:
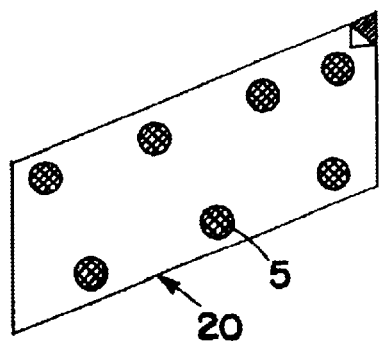
Figure 5:
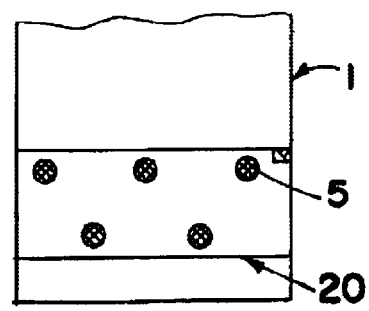

The invention is explained in more detail in the following, with reference to FIG. 1. In the enclosed drawings, there is shown:

FIG. 1 a vertical section of a height-reduced calibration instrument in accordance with the invention;

FIG. 2 a perspective representation of producing x-ray images with the aid of a calibration instrument in accordance with the prior art;

FIG. 3 a schematic vertical section of a calibration instrument in accordance with the prior art; and FIGS. 4 and 5 an adhesive foil comprising passive markers, and its attachment to an image recorder.

The calibration instrument C shown in FIG. 1 comprises substantially the same components as the calibration instrument C', explained above, in accordance with the prior art. The calibration instrument C is attached to the image recorder 1 of a C-arc x-ray device by the fixing device 2 which is fixedly connected to the first support 3. The markings 5 are attached on the fixing device 2 and to the first support 3, the calibration instrument being positionally detected and tracked in a medical navigation system with the aid of said markings. The support 4 is fixed to the support 3 by a detachable fixing means 6, for example a quick-release bayonet lock or a plug-in latching lock, said support 4—just like the support 3—circumscribing a plate which comprises localization structures, for example tungsten spheres or line structures.

The support 4 may be removed from the support 3, which considerably reduces the height of the calibration instrument, which then only comprises the support 3 while the patient x-ray is taken, and the clear width of the x-ray device is correspondingly increased. As opposed to the representation in FIG. 3, it can be seen in FIG. 1 that the markings 5 are now no longer attached to the two supports (13, 14 in FIG. 3) but to the support 3 and the fixing means 2 which also remain on the calibration instrument while the patient x-ray is taken.

The following activities are performed in operation with the calibration instrument in accordance with the invention. Firstly, a so-called "blank shot" is performed using the x-ray device, wherein the patient is not yet present in the radiation path, and for which the two supports 3, 4 comprising the localization structures are furthermore attached to the calibration instrument. The calibration information comprising the localization structures from two planes is stored. The blank shot can be performed once, but a number of blank shots can also be made, for example in the anterior-posterior direction, the lateral direction or in diagonal directions (X-images).

The support 4 is then removed from the support 3 via the quick-release lock 6, and the x-ray device is positioned over the patient.

The patient x-ray image to be calibrated is then produced, only those localization structures which are present on the support 3 being imaged on the x-ray image. The missing information from the second plane, i.e. from the localization structures of the support 4, are reconstructed, for which a number of options exist, four of which having been described above. If no deviations are determined for the localization structures of the support 3, the information can simply be taken from the blank shot. If there are deviations, the desired position of the localization structures of the removed support can be calculated or interpolated from the nature of the deviation, or re-calibration is performed with another blank shot in the same recording position.

In each case, the staff carrying out the treatment test the plausibility, purely visually or also with computer assistance, and establish whether the reconstruction of the localization data of the support 4 can be appropriate.

Once the plausibility has been successfully tested, the image is calibrated, and registration and x-ray-assisted navigation are performed, once the accuracy has again been verified.

FIGS. 4 and 5 also show how in accordance with another embodiment of the invention, markings—i.e. passive reflection markers 5—can be attached to the image recorder 1 of the x-ray device. Such an embodiment is particularly suitable when some or all of the supports comprising the localization structures are designed to be removable and are to be removed. A plastic film 20 is provided as a separate base layer which comprises a preferably detachable adhesive layer on one side and carries passive reflection markers 5. Specifically when pre-calibration has been performed, positioning information (the markers 5 on the adhesive film 20) can thus be directly attached to the image recorder/intensifier or detector, without further mechanical or construction conversions being necessary.

The present invention thus enables the height of the calibration instrument to be reduced, without restricting the accuracy of the x-ray navigation, which is significantly dependent on registration and therefore on the calibration instrument.

What is claimed is:

1. A method for calibrating x-ray image data for medical navigation, comprising the following steps:

providing a calibration instrument that is adapted to be positionally detected and tracked by a medical navigation system and has a plurality of localization structures that are detectable in x-ray images and are arranged on at least two spaced supports;

producing an x-ray image without a patient of the plurality of localization structures on the calibration instrument while the instrument is tracked by a medical navigation system;

registering the x-ray image without a patient in the navigation system using the plurality of localization structures;

removing at least one of the spaced supports, together with its localization structures, from the calibration instrument;

producing an x-ray image of a patient together with the calibration instrument with at least one support removed;

comparing the x-ray images of the calibration instrument to determine whether there is sufficient correspondence of the plurality of localization structures visible in the images.

2. The method as set forth in claim 1, wherein the x-ray image without a patient is produced first, to base-calibrate the x-ray image.

3. The method as set forth in claim 1, wherein a C-arc x-ray device is used to produce the x-ray images.

4. The method as set forth in claim 1, wherein when there is an insufficient correspondence between the x-ray images, another x-ray image of the calibration instrument without a patient is produced from the same position as when the patient x-ray image was taken, and the comparison step is repeated.

5. The method as set forth in claim 1, wherein when there is an insufficient correspondence between the x-ray images the, this is corrected by calculating, with computer assistance, the change in the imaging position from the change in the image data and determining new image data for the localizing structures of the removed support for the position of the patient x-ray.

6. The method as set forth in claim 1, wherein when there is an insufficient correspondence between the images from the two x-rays, a deviation value is determined, and if the deviation value does not exceed a predetermined limit, the positions of the removed localization structures from the x-ray image without a patient are used.

7. The method as set forth in claim 1, wherein when there is an insufficient correspondence between the x-ray images, deviation values are determined and the positions of the removed localization structures from the x-ray image without a patient are determined from the deviations, based on an interpolation rule determined beforehand.

8. A calibration instrument for calibrating x-ray image data for medical navigation, comprising:
   a device for arranging the calibration instrument in the radiation path of an x-ray device;
   at least two spaced supports on which localization structures are provided which are imaged on the x-ray images of the x-ray device; and
   markings for detecting the calibration instrument using a medical navigation system;
   wherein at least one of the supports is removable from the calibration instrument.

9. The calibration instrument as set forth in claim 8, wherein the localization structures are spherical or line structures, in particular made of tungsten, which may be imaged using x-rays.

10. The calibration instrument as set forth in claim 8, wherein it is arranged on an image recorder of the x-ray device.

11. The calibration instrument as set forth in claim 8, wherein the removable support is arranged on the non-removable support by means of a quick-release lock.

12. The calibration instrument as set forth in claim 11, wherein a rotating bayonet lock or a plug-type connection is used to fix the removable support.

13. The calibration instrument as set forth in claim 8, wherein the markings for detecting the calibration instrument using a medical navigation system are arranged on the non-removable support or on the device for arranging the calibration instrument in the radiation path of the x-ray device.

14. The calibration instrument as set forth in claim 8, wherein the markings are arranged on a separate base layer, such as a detachable adhesive film, which is attached to the x-ray device or to an image recorder.

15. A software system which, when it is running on a computer or is loaded on a computer, causes the computer to perform the following steps:
   producing an x-ray image without a the patient of a plurality of localization structures that are detectable in x-ray images and are arranged on at least two spaced supports on a calibration instrument while the instrument is tracked by a medical navigation system;
   registering the x-ray image without a patient in the medical navigation system using the plurality of localization structures;
   producing an x-ray image of a patient together with the calibration instrument with at least one of its spaced supports removed;
   comparing the x-ray images of the calibration instrument to determine whether there is sufficient correspondence of the plurality of localization structures visible in the images.

16. A computer program storage medium comprising the software system as set forth in claim 15.

* * * * *